Figure 1:
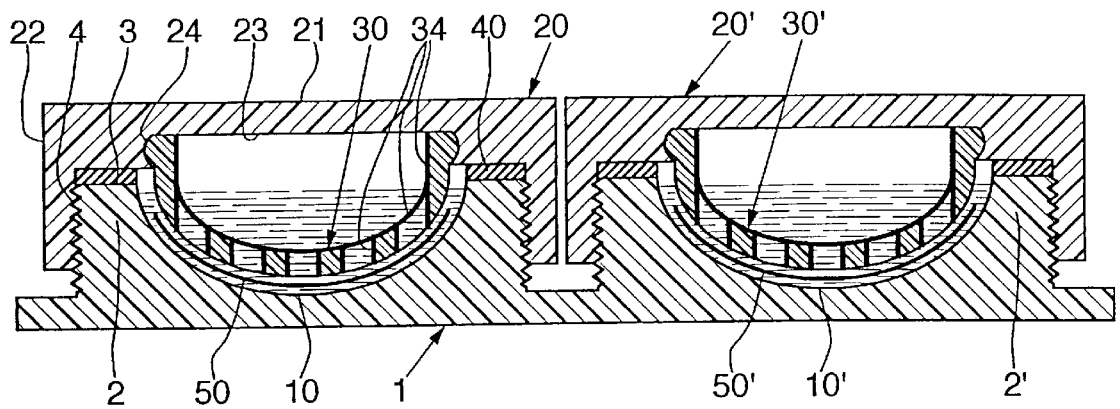

United States Patent

Bourset

[11] Patent Number: 6,086,823
[45] Date of Patent: Jul. 11, 2000

[54] FLAT CASE FOR DISINFECTING CONTACT LENSES

[75] Inventor: Claude Bourset, Creteil, France

[73] Assignee: Essilor International Compagnie Generale d'Optique, Charenton Cedex, France

[21] Appl. No.: 09/064,551

[22] Filed: Apr. 22, 1998

[30] Foreign Application Priority Data

Apr. 22, 1997 [FR] France ................................ 97 04937

[51] Int. Cl.[7] ........................................................ A61L 2/00
[52] U.S. Cl. .......................... 422/28; 422/30; 422/300; 422/301; 206/5.1; 134/901
[58] Field of Search ..................................... 422/300, 301, 422/30, 28; 206/5.1, 205; 134/901

[56] References Cited

U.S. PATENT DOCUMENTS

| | | |
|---|---|---|
| 4,392,569 | 7/1983 | Shoup . |
| 4,996,027 | 2/1991 | Kanner . |
| 5,129,999 | 7/1992 | Holland et al. . |
| 5,270,002 | 12/1993 | Neff et al. . |
| 5,320,997 | 6/1994 | Perlaky . |
| 5,431,879 | 7/1995 | Heyl et al. . |

FOREIGN PATENT DOCUMENTS

| | | |
|---|---|---|
| 0354876 | 2/1990 | European Pat. Off. . |
| 0389418 | 9/1990 | European Pat. Off. . |
| 0560728 | 9/1993 | European Pat. Off. . |
| WO 90/14848 | 12/1990 | WIPO . |

OTHER PUBLICATIONS

European Search Report date Jan. 12, 1998 (FR97/04937)(ESSR:011).

*Primary Examiner*—Robert J. Warden, Sr.
*Assistant Examiner*—Jennifer McNeil
*Attorney, Agent, or Firm*—Fulbright & Jaworski L.L.P.

[57] ABSTRACT

The flat case comprises a case body (1) comprising at least one wall (2) defining a disinfecting chamber (10) open at one end and intended to take a lens (50) to be disinfected, at least one removable cap (20) intended to be fixed on the open end of the chamber, at least one catalytic element secured to the cap (20) capable of being immersed in the disinfecting solution (10) and comprising a catalyst support and a catalyst (34) and at least one protective element (30) secured to the cap (20) having an end wall (32) provided with passages (33) for the disinfecting solution, forming a barrier between the lens (50) and the catalytic element, and at the same time holding the lens securely.

The invention has application to the disinfecting of contact lenses.

19 Claims, 4 Drawing Sheets

FLAT CASE FOR DISINFECTING CONTACT LENSES

The present invention relates in general to a flat case for disinfecting contact lenses and more specifically to a flat case of this kind in which the contact lenses are disinfected using a disinfecting solution, for example an oxidizing solution based on hydrogen peroxide and in which the disinfecting of the contact lenses and the neutralizing of the disinfecting solution take place simultaneously.

For disinfecting contact lenses, it is known for the contact lenses to be immersed in an oxidizing disinfecting solution based on hydrogen peroxide.

It goes without saying that it is extremely dangerous to insert into one's eye a contact lens which has just been taken out of a disinfecting hydrogen peroxide solution, for such a disinfecting solution is highly irritating to the eye. The disinfecting solution therefore needs to be neutralized before the contact lenses can be re-used. This neutralizing step is carried out conveniently by bringing a catalyst for breaking down the hydrogen peroxide into contact with the hydrogen peroxide solution.

Methods and assemblies for disinfecting contact lenses have also been proposed in which the contact lenses and the neutralizing catalyst are brought simultaneously into contact with a disinfecting solution, such as a hydrogen peroxide solution, in such a way that the reaction for neutralizing the disinfecting solution begins at the same time as the decontamination of the contact lenses.

Document EP-A-354 876 describes a method and an assembly for disinfecting contact lenses, in which the disinfecting of the contact lenses and the neutralizing of the disinfecting solution take place simultaneously. The disinfecting assembly in EP-A-354 876 comprises a cylindrical container and a detachable lid mounted on the container. A contact-lens and catalyst-block support secured to the cap hangs down into the container from this lid. Using this disinfecting assembly, the disinfecting solution, for example a hydrogen peroxide solution, is introduced into the container and then the block of catalyst and the contact lenses are introduced into the solution simultaneously when the lid is fixed onto the end of the container. In one embodiment in document EP-A-354 876, the block of catalyst is contained in a housing made in the contact lens support on one side of the baskets intended to hold the contact lenses. Such an embodiment leads to a complicated support for the contact lenses and for the block of catalyst.

In another embodiment in document EP-A-354 876, the block of catalyst is simply mounted at the lower end of the contact lens support, underneath the baskets which hold the contact lenses. With such a construction of the contact-lens and catalyst-block support, the block of catalyst is exposed to accidental contact when the lid and the contact-lens and catalyst-block support are taken out of the container.

Described in document EP-A-560 728 is an assembly for disinfecting contact lenses which comprises a cylindrical case body and a lid to which there is fixed a contact lens support. A catalyst is placed in the upper part of the case body on its internal surface. A stirrer, for example a bladed magnetic stirrer, is arranged in the bottom of the case body. During use, the case body is filled with an oxidizing solution of hydrogen peroxide to a level above the catalyst, then the contact lens support containing the contact lenses to be disinfected is introduced, fixing the lid onto the open end of the case body. Finally, the peroxide solution is stirred by turning the stirrer.

In this embodiment of document EP-A-560 728, the oxidizing disinfecting solution is initially introduced until it fills the case body to above the catalyst, so that the reaction of neutralizing the oxidizing solution begins before the contact lens support, and therefore the contact lenses to be disinfected, have been introduced into the case body. This means that there is a risk of the oxidizing solution being neutralized before the contact lens support and contact lenses to be disinfected have been introduced, to such an extent that the disinfecting oxidizing solution is no longer strong enough to disinfect the contact lenses properly.

Furthermore, in the embodiments of documents EP-A-354 876 and EP-A-560 728, the assemblies are relatively bulky and the catalyst is quite a way away from the lenses to be disinfected.

To ensure the most complete possible neutralization in the vicinity of the lenses, and mechanical stirring thereof under the effect of the bubbles of oxygen released during neutralization, it is desirable for the catalyst to be placed as close as possible to the lenses.

Document U.S. Pat. No. 5,431,879 describes a flat case for disinfecting contact lenses, comprising a case body comprising two accommodating housings and two caps for closing the accommodating housings. The lenses to be disinfected are held in the housing by two perforated lens holders fixed to the side walls of the housings. The lenses are sterilized and disinfected using solutions of anti-microbe agents. In one embodiment, elements for "neutralizing" the anti-microbe solution are arranged in the bottoms of the accommodating housings in order to extract the anti-microbe agent once sterilizing or disinfecting is finished.

The object of the present invention is therefore to provide a flat case for disinfecting contact lenses, in which the disinfecting of the contact lenses takes place at the same time as the neutralizing of the disinfecting solution, which is of a small size and simple construction, which protects the catalyst from accidental contact, particularly with the user's fingers or some other object, and which ensures that the neutralizing of the disinfecting solution does not start until the contact lenses have been immersed in the disinfecting solution.

Another object of the present invention is to provide a flat case for disinfecting contact lenses comprising means which appropriately hold the lenses and also provide protection against possible contact with the catalyst.

A further object of the present invention is to provide a flat case as defined hereinabove, in which the catalyst is placed as close as possible to the lenses to ensure the fullest possible neutralization of the disinfecting solution in the vicinity of the lenses and mechanical stirring thereof.

According to the invention, there is produced a flat case for disinfecting contact lenses having a convex face and a concave face using a disinfecting solution, for example an oxidizing solution based on hydrogen peroxide, which comprises:

- a case body comprising at least one wall defining a disinfecting chamber, preferably of hemispherical overall shape corresponding to the convex face of the lens, open at one end, intended to contain the disinfecting solution and to take a lens to be disinfected;
- at least one moveable cap intended to be fixed on the open end of the disinfecting chamber;
- at least one catalytic element for neutralizing the disinfecting solution secured to the cap, capable of being immersed in the disinfecting solution when the cap is fixed onto the case body, and comprising a catalyst support and a catalyst; and
- at least one protective element secured to the cap, having an end wall provided with passages for the disinfecting solution, forming a barrier between the lens and the catalytic element, while at the same time firmly holding the lens.

As a preference, the flat case comprises a case body comprising two distinct walls defining two separate disinfecting chambers, two caps, two catalytic elements and two protective elements.

The protective elements may be fixed inside the caps, for example by snap-fastening, or be molded as a single piece with the caps. The protective elements may also each be fixed to an annular seal, itself fixed, for example by bonding, inside the cap.

The protective elements secured to the caps may have any appropriate shape so long as they will be immersed in the disinfecting solution when the caps are fixed onto the case body and so long as they allow the disinfecting solution to circulate, and in particular allow the disinfecting solution to be in contact with all or most of the catalyst.

In a recommended embodiment of the invention, the protective elements which hold the lenses in the disinfecting chambers have an end wall of hemispherical overall shape, preferably corresponding to the concave face of the lenses.

In one embodiment of the invention, the catalyst support of the catalytic element consists of the unexposed or internal faces of the end wall of the protective element, that is to say all the surfaces other than the surface of the protecting element which faces the lens to be disinfected, and on which a layer of catalyst is deposited, this protecting the catalyst from any damaging contact.

In another embodiment of the invention, the catalyst support of the catalytic element consists of an attached element fixed to the inside of the protective element and comprising projecting elements directed toward the end wall of the protective element, and on which the catalyst is deposited. As a reference, the projecting elements have a height which increases from the periphery of the attached element toward its center, particularly when the end wall of the protective element is of hemispherical shape. This embodiment provides effective protection of the catalyst against any damaging contact.

By way of example, the end wall of the protective element, preferably of hemispherical shape, allowing a disinfecting solution to pass, may be formed of a perforated element, of a grid, of an element with spider arms or any other structure allowing the disinfecting solution to pass and to circulate, while holding the lens safely in the disinfecting chamber.

The catalysts for neutralizing oxidizing solutions based on hydrogen peroxide are well known in the art.

In the present invention, it is possible to use all catalysts for neutralizing disinfecting solutions, for example those based on hydrogen peroxide. Among the catalysts recommended, which can be used in the present invention, mention may be made of metals from the same group as platinum, such a platinum and paladium, particularly platinum black, and enzymes or catalases immobilized on a support, for example as described in documents EP-A-209 071 and WO-86 07 264.

The catalyst is generally deposited directly on the chosen surfaces of the catalyst support of the catalytic element.

When the catalyst of the catalytic element consists of a metal from the same group as platinum, it can be deposited by chemical deposition in vapor phase or by cathodic spraying.

The oxidizing disinfecting solutions based on hydrogen peroxide are well known in the state of the art and are described, among other sources, in French patent application no. 76 24 837.

The case body, the caps, the protective elements and the catalyst supports when they are distinct from the protection elements, are preferably made of plastic, for example of polyoxyphenylene, polypropylene or the like.

When the protective element has an end wall of recommended hemispherical shape with its convex face facing the end wall of the disinfecting chamber, not only does it hold the lens firmly and protect the catalyst effectively, but it also allows the catalyst, whether its support consists of the internal surfaces of the protective element or of an attached element, to be placed as close as possible to the concave face of the lens. It is thus possible to carry out more complete neutralization in the immediate vicinity of the lens. Furthermore, as the reaction for neutralizing the disinfecting solution produces a release of oxygen, the bubbles of oxygen produced in the immediate vicinity of the lens cause stirring of the disinfecting solution and of the lens, ensuring better disinfecting of the lens and at the same time better neutralizing of the disinfecting solution.

Figure 2:
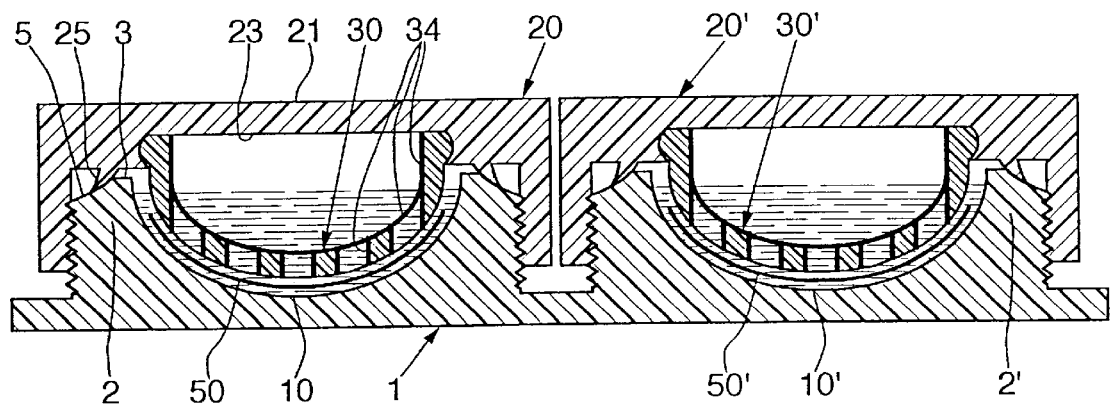
Figure 3:
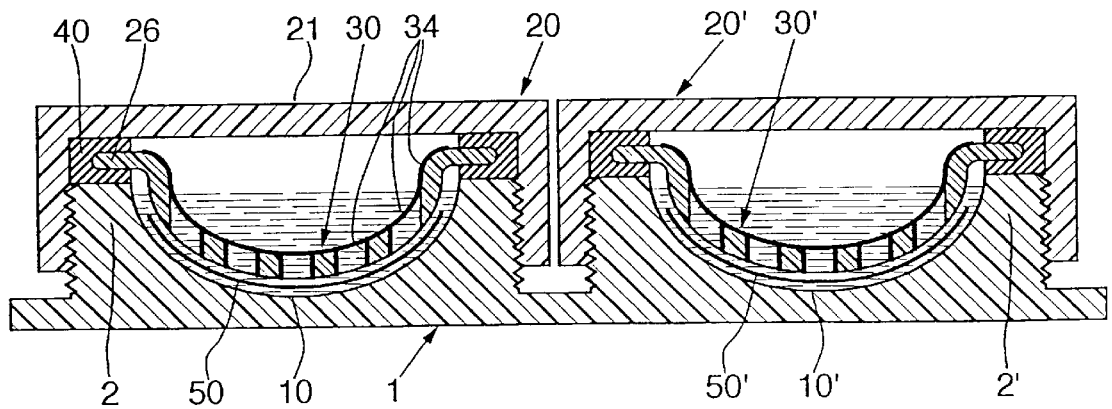
Figure 4:
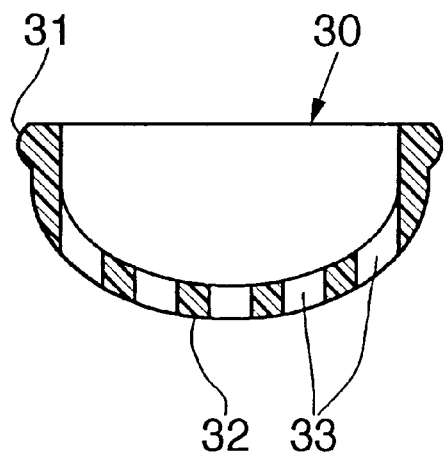
Figure 6:
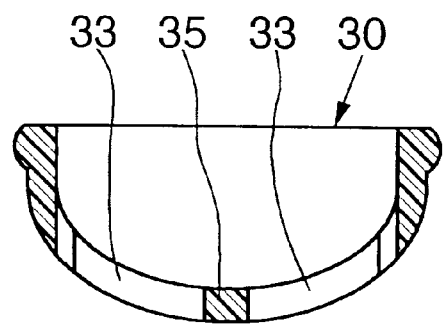
Figure 5:
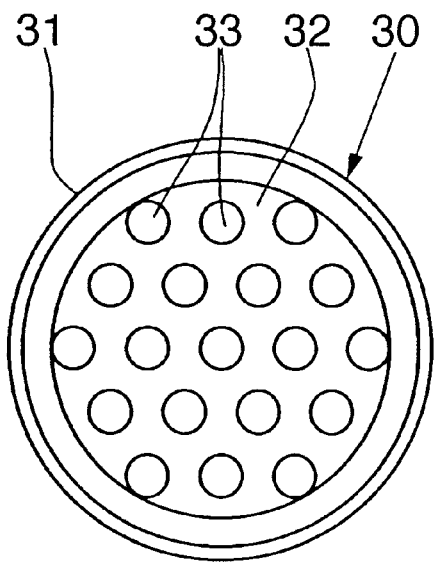
Figure 7:
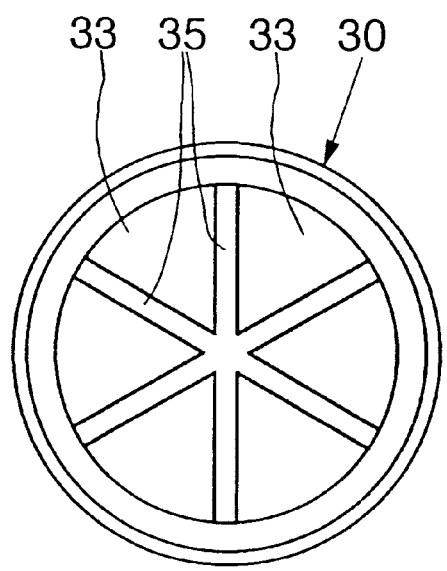
Figure 8:
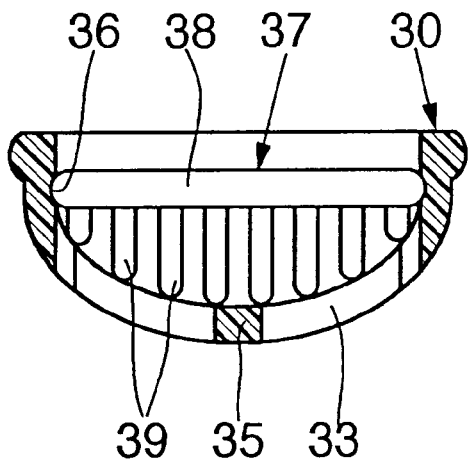
Figure 9:
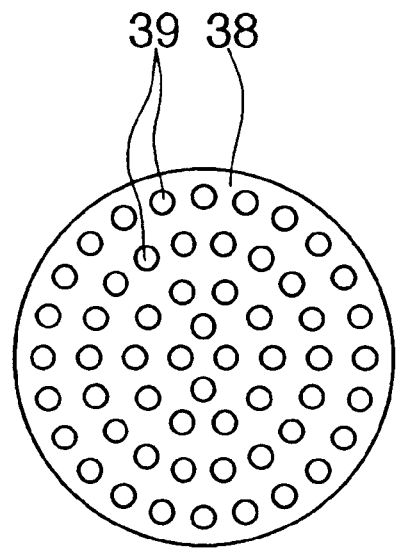
Figure 10:
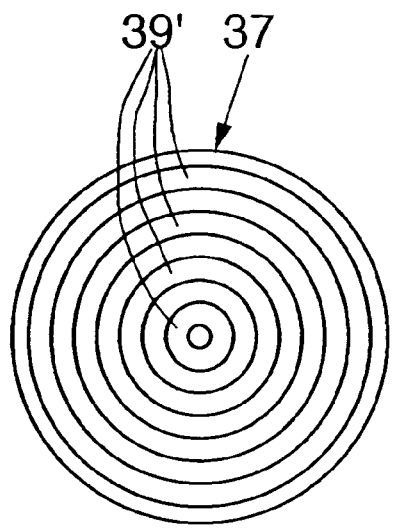
Figure 11:
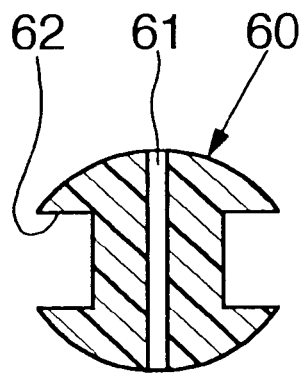

The remainder of the description makes reference to the appended figures which depict;

FIG. 1—a view in section of one embodiment of a flat case according to the invention;

FIG. 2—a view in section of a flat case similar to that of FIG. 1, in which sealing and degassing are provided by a flexible lip in place of the conventional annular seal;

FIG. 3—a view in section of another embodiment of a flat case, according to the invention;

FIG. 4—a view in section of a protective element of the flat case of FIG. 1;

FIG. 5—a view from below of the protective element of FIG. 4;

FIG. 6—a view in section of another embodiment of a protective element, according to the invention;

FIG. 7—a view from below of the protective element of FIG. 6;

FIG. 8—a view in section of yet another embodiment of a protective element, according to the invention, inside which there is fixed an attached element which acts as a catalyst support;

FIG. 9—a view from below of an attached element which acts as a catalyst support of FIG. 8;

FIG. 10—a view from below of an alternative form of the attached element which acts as a catalyst support in FIG. 8;

FIG. 11—a view in section of a degassing means, prior to fitting; and

Figure 12:
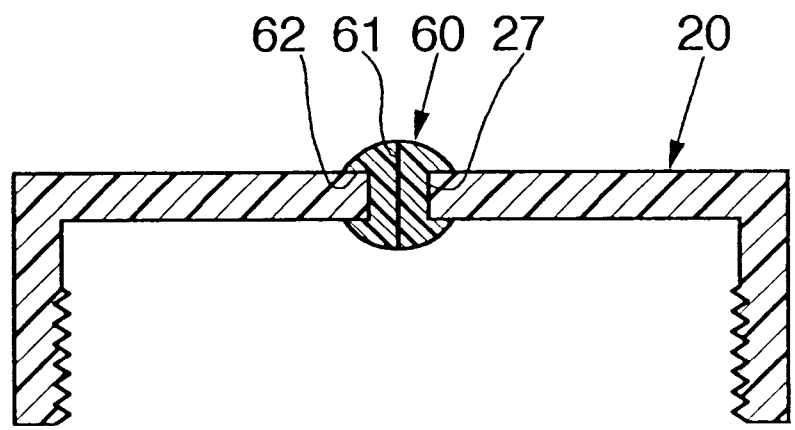

FIG. 12—a view in section of the degassing means of FIG. 11, fitted to the cap of the flat case.

Referring to the figures where the same reference numerals correspond to the same elements, and more particularly to FIG. 1, one embodiment of a flat case according to the invention has been depicted in section.

The flat case comprises a case body 1 comprising two walls 2, 2' defining two separate disinfecting chambers 10 and 10', two caps 20, 20' and two protective elements 30, 30'.

As the flat cases according to the invention and depicted in the figures comprise two identical halves, the description below will be given in conjunction with one of the halves of the flat case, it being obvious that the description of one half fully applies to the other half.

The disinfecting chamber 10 is preferably of hemispherical overall shape corresponding to the convex face of the lens to be disinfected, and is open at its upper end. Quite clearly the chamber 10 could have any other appropriate shape, such as a cylinder, a polygon, etc. The wall 2 defining the disinfecting chamber 10 ends, at the open end of the disinfecting chamber 10, in a flat annular end surface 3 and has a cylindrical external lateral surface 4 with a screw thread. The disinfecting chamber 10 is closed by a removable cap 20 which has an end wall 21 and a cylindrical side wall 22. The internal surface of the side wall 22 of the cap 20 has a screw thread intended to cooperate with the screw thread on the external lateral surface 4 of the wall 2 of the disinfecting chamber 10 to hold the cap firmly on the chamber. A cylindrical recess 23, the side wall of which forms an annular groove 24 is formed at the center of the end wall 21 inside the cap 20.

A protective element 30 is fixed inside the cap 20 by snap-fastening into the central recess 23 in the end wall 21 of the cap and hangs down inside the cap.

As best seen in FIG. 4, this protective element has the overall shape of a hemispherical basket, preferably following the curvature of the concave face of the lens to be disinfected, and the open upper end of which comprises an annular rim 31 which complements the annular groove 24 of the recess 23 in the end wall 21 of the cap 20 allowing the protective element 30 to be snap-fastened inside the cap 20. The protective element 30 is provided in its curved end wall 32 with passages 33 which, in the embodiment depicted as can be seen in FIG. 5, are simple holes.

A catalyst 34 is deposited on the internal surface and, possibly, on the lateral walls of the passages 33 of the protective element 30 which thus acts as a support for this catalyst 34. Thus, the catalyst 34 is protected from any damaging contact, for example with the user's fingers or with the lens during the disinfecting operation.

Although the passages 33 have been depicted in the form of circular holes, these passages 33 may have any appropriate shape whatsoever, for example polygonal, oval, etc.

Likewise, the number of passages 33 is not critical so long as it allows sufficient circulation of the disinfecting solution and effective contact with the catalyst 34.

As shown in FIG. 1, an annular seal 40, for example a silicone or polybutadiene seal, is placed between the cap 20 and the flat annular end surface 3 of the wall 2 defining the disinfecting chamber 10.

The cap 20 further comprises a degassing means well known in the art. For example, this degassing means may simply be a hole made in the end wall 21 or alternatively an opening made in this end wall 21 and closed by a gas-permeable, particularly oxygen-permeable, or perforated membrane.

FIGS. 11 and 12 depict a degassing means which may advantageously be used with the flat case according to the invention. Referring to FIG. 11, which is a sectional view through the degassing means before it is fitted on the cap 20 of the case, the degassing means consists of a sleeve 60 made of a flexible material, for example a natural rubber or a synthetic elastomer. This flexible sleeve 60, for example of cylindrical overall shape, has a passage 61. A groove, generally a circular groove, 62 is also formed in the lateral wall of the sleeve 61.

As FIG. 12 shows, the sleeve is arranged in a generally circular opening 27 formed in the end wall 21 of the cap 20 of the case, so that the sleeve 60 is held in the cap 20 by the engagement of the edges of the opening 27 of the end wall 21 of the cap 20 in the circular groove 62. Furthermore, the size of the opening 27 in the end wall 21 of the cap is such that once the sleeve 60 is placed in the opening 27, the sleeve finds itself compressed and the walls of the passage 61 come into contact, making it impervious to liquids. Under the effect of the pressure of the gases generated during disinfection, and because of the flexible and elastic nature of the material of which the sleeve 60 is made, the walls of the passage 61 part, allowing the gases to escape.

The way in which the flat disinfecting case according to the invention and depicted in FIG. 1 works will now be described.

When the user wishes to disinfect his contact lenses, he unscrews the lids 20 and 20' to detach them from the case body 1 together with the protective elements 30 and 30' which also act as supports for the catalyst. He then introduces his contact lenses 50, 50', convex faces downward, into the disinfecting chambers 10, 10'. He fills the disinfecting chambers 10, 10' with disinfecting solution, for example a hydrogen peroxide solution, then he screws the caps 20, 20' carrying the protective elements 30, 30' onto the chambers 10, 10'. As the protective elements 30, 30' hang down inside the cap, they become immersed in the disinfecting solution. As soon as the disinfecting solution comes into contact with the catalyst deposited on the internal surfaces of the protective elements 30, 30', the neutralization reaction begins. Because of the hemispherical shape of the protective elements 30, 30' corresponding to the concave face of the lenses 50, 50' to be disinfected, the lenses are held firmly in the disinfecting chambers 10, 10' and the catalyst 34 lies as close as possible to the lenses and the neutralization reaction thus takes place as close as possible to the surfaces of the lenses 50, 50'. During the neutralization reaction, oxygen is given off, as the oxygen bubbles being formed as close as possible to the lenses 50, 50' make sure that the solution circulates near the lenses and stirs up the lenses 50, 50', which increases the effectiveness of the disinfecting solution at the lenses. Furthermore, because of the presence of the passages in the catalytic elements 30, 30', the circulation of disinfecting solution and the area of contact with the catalyst and therefore the effectiveness of the neutralization are improved.

Referring now to FIG. 2, this depicts another embodiment of a flat case according to the invention, which differs from the flat case of FIG. 1 only in the means which provide the seal between the cap 20 and the case body 1.

In this embodiment, the seal 40 of the case of FIG. 1 is replaced by a flexible annular lip 25 which projects from the internal surface of the end wall 21 of the cap 20 and surrounds the central recess 23. This lip 25 cooperates with the annular end surface 3 of the wall 2 defining the disinfecting chamber 10.

As can be seen in FIG. 2, the flexible annular lip 25 preferably has a cross section with the overall shape of a triangle fixed by its base to the end wall 21 of the cap 20.

The annular end surface 3 of the wall 2 comprises a chamfered annular bearing surface 5 against which the lip 25 of the cap is pressed elastically when the cap 20 is screwed onto the open end of the disinfecting chamber 10.

As a preference, the internal lateral wall of the lip 25 is slightly curved and the annular bearing surface 5 has a complementary curvature, this improving sealing.

In addition, on account of its flexibility, the lip 25 allows the degassing of the disinfecting chamber 10, the gases, once they have got past the lip 25, being removed either via the screw threads or via means similar to those described in conjunction with the embodiment of FIG. 1 and formed in the cap 20 outside the lip 25.

The flat case of the embodiment of FIG. 2 works in the same way as the embodiment of FIG. 1.

FIG. 3 depicts yet another embodiment of a flat case according to the invention. This flat case, the overall construction of which is similar to that of the flat case of the embodiment of FIG. 1, differs from this embodiment in that the protective element 30 is not fixed directly to the cap 20 but is fixed by a thin annular rim 26 to the seal 40 which is itself fixed inside the cap 20, for example by bonding, to the end wall 21 of the cap 20. In this case, it is unnecessary to provide a central recess in the end wall 21 of the cap 20.

The flat case of this embodiment works in the same way as in the embodiments of FIGS. 1 and 2.

FIGS. 6 to 9 deal with alternative forms of protective element which can be used in the embodiments of flat case of FIGS. 1 and 2.

Referring to FIGS. 6 and 7, these depict a protective element 30, the hemispherical end wall 32 of which is formed by spider arms 35, the passages 33 being formed by the spaces between the spider arms 35.

The catalyst, like in the protective element described previously, is deposited on the internal surfaces, and possibly lateral surfaces, of the spider arms 31, the protective element also in this case acting as a catalyst support.

FIG. 8 depicts an alternative form in which the catalyst support is formed of an attached element 37 fixed to the inside of the protective element 30. The protective element 30, in the case depicted, is similar to the protective element of FIG. 6, but on its internal surface close to its open upper end has an annular groove 36. The attached element 37 which acts as a catalyst support consists of a disk 38 which on one of its faces has fingers 39. This attached element 37 is placed inside the protective element 30 in such a way that the fingers 39 point toward the end wall 32 of the protective element 30, and it is held in the protective element 30 by snap-fastening the periphery of the disk 38 into the annular groove 36 of the protective element 30.

As FIG. 9 shows, the fingers 39 may be arranged in concentric circles and preferably have a height which increases from the periphery of the disk 38 toward its center so as to match the hemispherical shape of the protective element 30 when the attached element 37 acting as a catalyst support is placed in the protective element 30.

In this embodiment, the catalyst is deposited on the external surfaces of the fingers 39 in order to achieve the catalytic element.

With such a structure, the catalyst is completely protected from any damaging contact by the protective element, while being extremely close to the lenses to be disinfected during use.

FIG. 10 is a view from below of another embodiment of an attached element 37, in which the fingers 39 have been replaced by concentric circular ridges 39'. Preferably, in this embodiment too, the ridges 39' have heights which increase from the periphery of the disk as far as its center, so as to match the hemispherical shape of the protective element 30.

In this last embodiment, the catalyst is fixed to the surfaces of the ridges 39'.

Although FIGS. 4 to 8 depict protective elements for producing a flat case according to FIGS. 1 or 2, these protective elements can also be adapted to the embodiment of FIG. 3.

Likewise, the protective element 30 of the embodiment of FIG. 4 can be used with an attached element 37 acting as a catalyst support like in the embodiment of FIG. 8.

What is claimed is:

1. A substantially flat case for disinfecting contact lenses comprising:

a case body comprising at least one wall having a substantially hemispherical shape corresponding to the convex face of the lens and partly defining a lens disinfecting chamber, the disinfecting chamber having at least one open end;

at least one removable cap configured to be fixed on the open end of the disinfecting chamber;

at least one catalyst positioned to be immersed in disinfecting solution when the cap is fixed to the case body during use; and at least one protective element secured to the cap having passages through which disinfecting solution can pass during use, the contact lens being disposed, during use, between said at least one wall of substantially hemispherical shape and the protective element so that the protective element forms a barrier between the lens and the catalyst while at the same time holding the lens securely during use.

2. The case of claim 1, wherein the protective element has a substantially hemispherical shape that corresponds to the concave face of the lens during use.

3. The case of claim 1, wherein the protective element fixes to the cap during use by snap-fastening.

4. The case of claim 1, wherein the protective element is fixed during use to an annular seal that is fixed to the cap during use.

5. The case of claim 1, wherein the cap comprises a flexible annular sealing lip configured to engage on a chamfered annular bearing surface of the wall defining the disinfecting chamber during use.

6. The case of claim 1, wherein the passages in the protective element are holes.

7. The case of claim 1, wherein the protective element comprises a substantially hemispherical end wall formed of spider arms, and the passages are defined by spaces between the spider arms.

8. The case of claim 1, wherein the catalyst is on a catalyst support.

9. The case of claim 8, wherein the catalyst support comprises unexposed surfaces of the protective element, and the catalyst is deposited on said surface.

10. The case of claim 8, wherein the catalyst support is an attached element fixed inside the protective element.

11. The case of claim 10, wherein the attached element comprises a support disk having at least one face that comprises projecting elements to which the catalyst is fixed, the attached element fixed to the protective element so that the projecting elements project toward an end wall of the protective element.

12. The case of claim 11, wherein the projecting elements have a height that increases from the periphery of the support disk toward its center.

13. The case of claim 11, wherein the projecting elements are fingers.

14. The case of claim 11, wherein the projecting elements are circular ridges.

15. The case of claim 1, comprising two walls defining two disinfecting chambers, two caps, two protective elements, and two catalysts.

16. The case of claim 1, further defined as having a substantially flat configuration.

17. A substantially flat case for disinfecting contact lenses comprising:

a case body comprising at least one wall having a substantially hemispherical shape corresponding to the convex face of the lens and partly defining a disinfecting chamber which is open at one end and adapted to receive a lens to be disinfected during use;

at least one removable cap adapted to be fixed on the open end of the disinfecting chamber during use;

at least one catalyst for neutralizing disinfecting solution during use, capable of being immersed in disinfecting solution when the cap is fixed to the case body during use, wherein the catalyst is on a catalyst support; and at least one protective element secured to the cap, having an end wall provided with passages for the disinfecting solution during use, the contact lens being disposed, during use, between said at least one wall of substantially hemispherical shape and the protective element so that the protective element forms a barrier between the lens and the catalyst while at the same time holding the lens securely during use.

18. A method for disinfecting a contact lens comprising:

obtaining a case comprising:

- a case body comprising at least one wall having a substantially hemispherical shape corresponding to the convex face of the lens and partly defining a lens disinfecting chamber, the disinfecting chamber having at least one open end;
- at least one removable cap configured to be fixed on the open end of the disinfecting chamber;
- at least one catalyst positioned to be immersed in disinfecting solution when the cap is fixed to the case body during use; and
- at least one protective element secured to the cap having passages through which disinfecting solution can pass during use;

placing a contact lens to be disinfected in the case with its convex face resting on the substantially hemispherical shape wall;

placing disinfecting solution in the case;

fixing the cap to the case body so that the protective element forms a barrier between the lens and the catalyst while at the same time holding the lens securely; and disinfecting the lens.

19. The method of claim 18, wherein the disinfecting solution is an oxidizing solution based on hydrogen peroxide.

* * * * *